United States Patent
Wei et al.

(10) Patent No.: US 11,447,440 B2
(45) Date of Patent: Sep. 20, 2022

(54) TREPROSTINIL MONOHYDRATE CRYSTALS AND METHODS FOR PREPARATION THEREOF

(71) Applicant: CHIROGATE INTERNATIONAL INC., Yangmei (TW)

(72) Inventors: Shih-Yi Wei, Yangmei (TW); Jian-Bang Jheng, Yangmei (TW); Chun Hsieh, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 17/083,673

(22) Filed: Oct. 29, 2020

(65) Prior Publication Data

US 2022/0135511 A1 May 5, 2022

(51) Int. Cl.
*C07C 59/13* (2006.01)
*C07C 51/43* (2006.01)
*C07C 51/47* (2006.01)

(52) U.S. Cl.
CPC .............. *C07C 59/13* (2013.01); *C07C 51/43* (2013.01); *C07C 51/47* (2013.01); *C07B 2200/13* (2013.01)

(58) Field of Classification Search
CPC ......... C07C 59/13; C07C 51/43; C07C 51/47; C07C 2603/14; C07C 51/412; C07C 59/72; C07B 2200/13
See application file for complete search history.

(56) References Cited

U.S. PATENT DOCUMENTS

| | | |
|---|---|---|
| 6,521,212 B1 | 2/2003 | Cloutier et al. |
| 6,756,033 B2 | 6/2004 | Cloutier et al. |
| 8,232,316 B2 | 7/2012 | Phares et al. |
| 9,822,057 B2 | 11/2017 | Phares et al. |
| 10,167,247 B2 | 1/2019 | Phares et al. |
| 2015/0148414 A1 | 5/2015 | Malinin et al. |
| 2018/0072649 A1* | 3/2018 | Phares .................. A61P 11/06 |

FOREIGN PATENT DOCUMENTS

WO  2009/137066  11/2009

OTHER PUBLICATIONS

Robert M. Moriarty, et al: The Intramolecular Asymmetric Pauson-Khand Cyclization as a Novel and General Stereoselective Route to Benzindene Prostacyclins: Synthesis of UT-15 (Treprostinil): J. Org. Chem. 69, 1890-1902 (2004).

* cited by examiner

*Primary Examiner* — Yevgeny Valenrod
*Assistant Examiner* — Blaine G Doletski
(74) *Attorney, Agent, or Firm* — Ladas & Parry LLP

(57) ABSTRACT

Novel crystalline forms of Treprostinil monohydrate, a mixture including the same, and preparation methods thereof.

10 Claims, 11 Drawing Sheets

TREPROSTINIL MONOHYDRATE CRYSTALS AND METHODS FOR PREPARATION THEREOF

FIELD OF THE INVENTION

The present invention relates in general to solid forms of benzindene prostacyclin derivatives, and in particular, to novel crystalline forms of Treprostinil monohydrate and preparation methods thereof.

BACKGROUND OF THE INVENTION

Treprostinil (UT15) is a synthetic analogue of benzindene prostacyclin having the following structural formula:

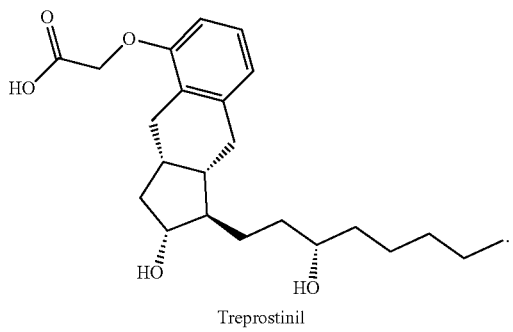 [SMILES: CCCCC[C@H](O)CC[C@@H]1[C@H]2Cc3cccc(OCC(=O)O)c3C[C@H]2C[C@H]1O]

Treprostinil

Treprostinil is used for treating patients with pulmonary arterial hypertension (PAH) to improve exercise capacity, and can be prepared in various dosage forms in medicaments, and administered orally, by inhalation or by injection. US 2015/148414 reveals that the infused Tyvaso® (Treprostinil) is a long acting pulmonary vasodilator providing significantly lower plasma levels for treating pulmonary hypertension. Remodulin® (Treprostinil sodium) injection is another formulation approved by the U.S. Food and Drug Administration (FDA) for treating PAH. Remodulin® is a sterile sodium salt formulated for subcutaneous or intravenous administration. U.S. Pat. No. 8,232,316 discloses that the oral administration of Treprostinil diethanolamine can increase the oral bioavailability and circulating concentrations of Treprostinil. U.S. Pat. Nos. 6,521,212 and 6,756,033 also disclose the treatment of pulmonary hypertension by inhalation of Treprostinil.

Treprostinil is a high polarity compound containing one carboxylic acid (—COOH) and two hydroxyl (—OH) functional groups, and is very easily esterified with alcohols, including Treprostinil itself, to form dimers or esters thereof. WO 2009/137066 discloses the preparation of a comparative anhydrous Treprostinil crystal (Lot No. 01 A07002). The anhydrous Treprostinil crystal initially contains 0.5% Treprostinil dimers (0.2% 750W93+0.3% 751W93), which might be generated during the high-temperature production process. WO 2009/137066 also describes the dimers as continuing to form in standing anhydrous Treprostinil at 25° C. according to the stability tests, and the dimer formation is increased at higher temperature and is negligible at 5° C. Hence. WO 2009/137066 provides a Treprostinil monohydrate crystal. In comparison with the anhydrous Treprostinil crystal, the Treprostinil monohydrate crystal is more stable and can be stored at room temperature over a long period of time. The dimer formation of the Treprostinil monohydrate crystal is almost negligible according to the accelerated stability tests at 25° C., 30° C. and 40° C. for 6 months (Lot No. 01M07033). However, esterification impurities of Treprostinil would be generated during the crystallization of Treprostinil monohydrate by using alcohol solvents. The Treprostinil monohydrate crystals (Lot No. D-1007-089, container 2) prepared from an ethanol-water system with a purity of about 99.5% initially comprises 0.2% Treprostinil ethyl ester or UT-15 ethyl ester, 0.1% 750W93, 0.04% 751W93, and 0.05% impurity 1 and <0.05% impurity 2 as disclosed by WO 2009/137066. The Treprostinil monohydrate crystals (Lot No. 01M07033) with a purity of about 99.6% initially comprises 0.1% 3AU90, 0.2% Treprostinil ethyl ester or UT-15 ethyl ester, 0.08% 750W93 and <0.05% 751W93 as disclosed by WO 2009/137066.

In conjunction with the above issue, U.S. Pat. No. 9,822,057 and U.S. Ser. No. 10/167,247 disclose another method for preparing the Treprostinil monohydrate by using solvents other than ethanol, so as to avoid generating Treprostinil ethyl ester. U.S. Pat. No. 9,822,057 and U.S. Ser. No. 10/167,247 further disclose two crystalline forms of the Treprostinil monohydrate (Form A and Form B), as shown in FIG. 1 and FIG. 3, respectively. However, the preparation processes of crystalline Treprostinil monohydrate Form A and Form B are complex. The crystalline Treprostinil monohydrate Form A is prepared from a slurry specimen (comprising 500 mg Treprostinil with 3.0 ml 1,4-dioxane/water 1:1 v/v solution), which is needed to be left rotating on a wheel at room temperature for a long period of time (about three days) and filtered to isolate the solid. The solid is then crushed step by step into smaller pieces for further drying (about one day) to obtain crystalline Treprostinil monohydrate Form A. The crystalline Treprostinil monohydrate Form B is also prepared from a slurry specimen (comprising 1019 mg Treprostinil with 3.5 ml methanol and 3.5 ml water), which is needed to be placed in a capped vial at room temperature for a long period of time (about three days) and filtered to isolate the solid. The solid is then crushed step by step into smaller pieces for further drying (about 44 hours) to obtain crystalline Treprostinil monohydrate Form B. After approximately two days of drying, the water content of crystalline Treprostinil monohydrate Form B is still 12.24%. It appears that the water content of crystalline Treprostinil monohydrate Form B is not easily reduced to about 4.41% (one mole of water molecules in Treprostinil calculates to 4.41% by weight). The preparation methods disclosed by U.S. Pat. No. 9,822,057 and U.S. Ser. No. 10/167,247 can obtain the crystalline Treprostinil monohydrate Form A and Form B with fewer impurities; however, these complex preparation processes are not suitable for industry scale operations.

Consequently, there is a demand for preparing Treprostinil monohydrate crystals in an efficient and economical way, where undesirable impurities can also be effectively avoided during the preparation processes.

SUMMARY OF THE INVENTION

Based on the above, the inventor performed a series of experiments, and surprisingly found that the addition of phosphoric acid to a basic Treprostinil aqueous solution can obtain Treprostinil monohydrate crystals in a precise and simple manner. The method can be implemented at room temperature in a relatively short time (four to six hours) without using organic solvents (e.g., alcohols), which can drastically reduce the possibility of the formation of Treprostinil dimers and/or unwanted esterification impurities. The obtained Treprostinil monohydrate crystals with high yield (>90%) and high purity (>99%) can also be easily filtered and dried.

According to one aspect, the present invention provides two novel crystalline forms of Treprostinil monohydrate, "Form I and Form II," and methods for the preparation thereof.

In one embodiment, the present invention provides a method for preparing a crystalline Treprostinil monohydrate Form I, which comprises providing a basic Treprostinil aqueous solution; adding phosphoric acid to the basic Treprostinil aqueous solution until the aqueous solution becomes acidic, having a pH value of about 2 to about 6, wherein a decreasing rate of the pH value is less than about 0.2 per minute; and stirring until a precipitate is formed. The method further comprises the steps of filtering out the precipitate and/or adding water for rinsing the precipitate, thereby isolating the crystalline Treprostinil monohydrate Form I, and optionally drying the crystalline Treprostinil monohydrate Form I.

In one embodiment, the present invention provides a crystalline Treprostinil monohydrate Form I having an X-ray power diffraction (XRPD) pattern exhibiting its two strongest characteristic peaks at the following 2θ reflection angles: 5.43±0.2°, and 10.87±0.2°. The crystalline Treprostinil monohydrate Form I is substantially free of any other form of crystalline Treprostinil.

In one embodiment, the present invention provides a crystalline Treprostinil monohydrate Form I having a differential scanning calorimetry (DSC) thermogram pattern comprising two major endothermic peaks, one with a peak onset temperature of 65.9±2° C. and a peak maximum of 79.2±2° C., and the other with a peak onset temperature of 123.2±2° C. and a peak maximum of 125.1±2° C.

In one embodiment, the present invention provides a method for preparing a crystalline Treprostinil monohydrate Form II, which comprises providing a basic Treprostinil aqueous solution; adding phosphoric acid to the basic Treprostinil aqueous solution until the aqueous solution becomes acidic, having a pH value of about 2 to about 6, wherein a decreasing rate of the pH value is more than about 0.6 per minute; and stirring until a precipitate is formed. The method further comprises the steps of filtering out the precipitate and/or adding water for rinsing the precipitate, thereby isolating the crystalline Treprostinil monohydrate Form II, and optionally drying the crystalline Treprostinil monohydrate Form II.

In one embodiment, the present invention provides a crystalline Treprostinil monohydrate Form II having an XRPD pattern exhibiting its two strongest characteristic peaks at the following 2θ reflection angles: 5.19±0.2° and 10.40±0.2°. The crystalline Treprostinil monohydrate Form II is substantially free of any other form of crystalline Treprostinil.

In one embodiment, the present invention provides a crystalline Treprostinil monohydrate Form II having a DSC thermogram pattern comprising two major endothermic peaks, one with a peak onset temperature of 58.8±2° C. and a peak maximum of 73.8±2° C., and the other with a peak onset temperature of 123.9±2° C. and a peak maximum of 125.1±2° C.

According to another aspect, the present invention provides a mixture comprising crystalline Treprostinil monohydrate Form I and crystalline Treprostinil monohydrate Form II, which has an XRPD pattern exhibiting its jointly characteristic peaks at the following 2θ reflection angles: 5.26±0.2°, 13.20±0.2°, and 16.25±0.2°, and its separated characteristic peaks at 10.65±0.2° and 12.20±0.2° belonging to Form I and at 10.36±0.2°. 11.61±0.2°, and 12.60±0.2° belonging to Form II. The mixture of Treprostinil monohydrate crystals comprises at least about 10% of Form I or at least about 10% of Form II. The mixture of Treprostinil monohydrate crystals is substantially free of any other form of crystalline Treprostinil.

In one embodiment, the present invention provides a method for preparing a mixture comprising crystalline Treprostinil monohydrate Form I and crystalline Treprostinil monohydrate Form II, which comprises providing a basic Treprostinil aqueous solution; adding phosphoric acid to the basic Treprostinil aqueous solution until the aqueous solution becomes acidic, having a pH value of about 2 to about 6, wherein a decreasing rate of the pH value is more than about 0.2 and less than about 0.6 per minute; and stirring until a precipitate is formed. The method further comprises the steps of filtering out the precipitate and/or adding water for rinsing the precipitate, thereby isolating the mixture comprising crystalline Treprostinil monohydrate Form I and crystalline Treprostinil monohydrate Form II.

DETAILED DESCRIPTION OF THE INVENTION

Figure 1:
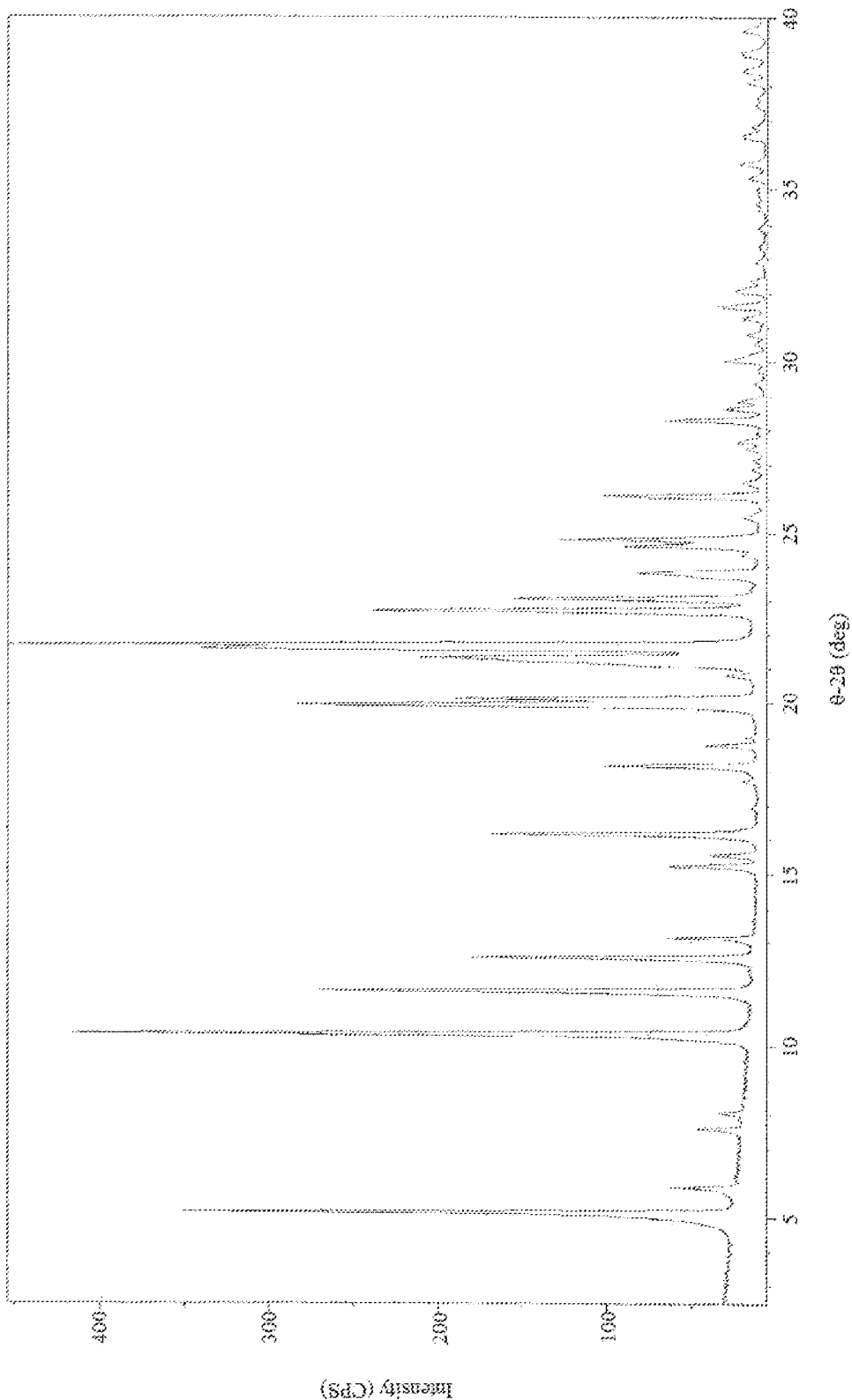
FIG. 1 shows an X-ray power diffraction (XRPD) pattern of the crystalline Treprostinil monohydrate Form A.

When used herein, the term "substantially free of any other form of crystalline Treprostinil," or the like, means that the compound or mixture in question does not contain more than 0.5%, 0.4%, 0.3%, 0.2% or 0.1% of any other form of crystalline Treprostinil.

Preparation of Basic Treprostinil Aqueous Solution

A basic Treprostinil aqueous solution can be prepared by any suitable processes. A typical synthesis process of Treprostinil is shown in the following Scheme A:

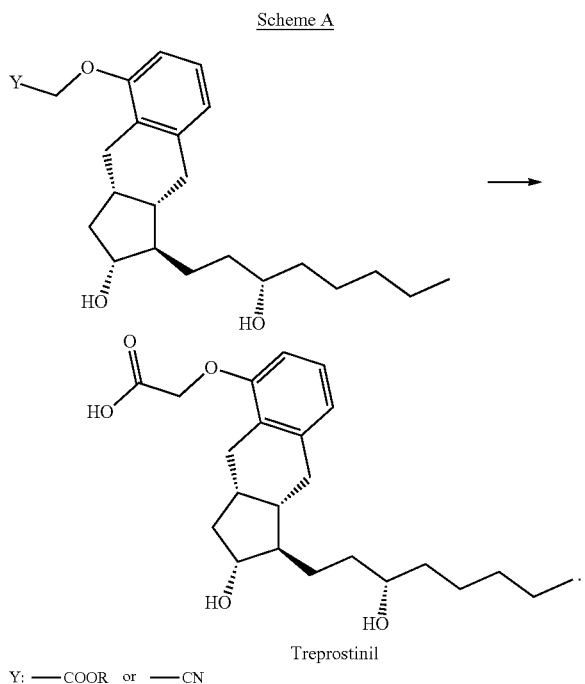

Y: —COOR or —CN

Treprostinil can be obtained from the hydrolysis of Treprostinil ester or Treprostinil nitrile by adding a base, such as potassium hydroxide, sodium hydroxide and lithium hydroxide, to an organic solvent, such as methanol, ethanol, isopropyl alcohol, tetrahydrofuran and acetone, with water, or by adding hydrolase to a base buffer aqueous solution. After the hydrolysis reaction, the prepared Treprostinil is dissolved in an aqueous phase, and the residual organic solvent can be removed by extraction or concentration. When using hydrolase, the hydrolase can be removed by filtration. The prepared aqueous solution without organic solvents and hydrolases is the so called "basic Treprostinil aqueous solution" as mentioned above. In some embodiments, the pH value of the basic Treprostinil aqueous solution is not limited to values between about 7 to about 14, about 8 to about 13, about 9 to about 12, about 10 to about 11, or about 8 to about 12.

In one embodiment, the basic Treprostinil aqueous solution can be obtained by dissolving Treprostinil alkali salt, such as Treprostinil sodium, Treprostinil potassium and Treprostinil lithium, or Treprostinil amine salt, such as Treprostinil diethanolamine and Treprostinil tromethamine, in water.

In one embodiment, the basic Treprostinil aqueous solution can be obtained by dissolving Treprostinil in an organic solvent, such as ethyl acetate, and then extracting by a basic aqueous solution, such as a sodium hydrogen carbonate aqueous solution. The separated aqueous phase is therefore gathered as the basic Treprostinil aqueous solution.

Acidifying the Basic Treprostinil Aqueous Solution to Obtain Treprostinil Solids In the prior art, such as WO 2009/137066 and *J. Org. Chem.* 69, 1890-1902 (2004), the prepared Treprostinil obtained by adding hydrochloric acid to the basic Treprostinil aqueous solution is a yellow gummy solid or sticky liquid. Hence, the prior arts have to use an organic solvent for extracting the gummy or sticky Treprostinil suspended in an aqueous solution. Surprisingly, the inventor discovered that the Treprostinil obtained by adding phosphoric acid to the basic Treprostinil aqueous solution is a white crystalline solid, which can be easily filtered and dried, as compared with the gummy solid or sticky liquid. The white crystalline solid of Treprostinil is in a monohydrated form confirmed by thermogravimetric analysis (TGA) and Karl Fischer titration. Moreover, the obtained Treprostinil monohydrate shows two novel crystalline forms (Form I and Form II) confirmed by X-ray powder diffraction (XRPD). The inventor also found that the slow addition rate of phosphoric acid is conducive to the formation of Form I, while the quick addition rate is conducive to the formation of Form II.

Crystalline Treprostinil Monohydrate Form I and Preparation Thereof

In an embodiment, the method for preparing crystalline Treprostinil monohydrate Form I or Treprostinil monohydrate Form I crystal comprises the steps of
(a) providing a basic Treprostinil aqueous solution;
(b) slowly adding phosphoric acid dropwise to the basic Treprostinil aqueous solution until the aqueous solution becomes acidic, having a pH value of about 2 to about 6, wherein the pH value of the aqueous solution is decreased at a rate of less than about 0.2 per minute;
(c) stirring until a precipitate is formed;
(d) filtering out the precipitate and/or adding water for rinsing the precipitate, thereby isolating the crystalline Treprostinil monohydrate Form I; and
(e) optionally drying the crystalline Treprostinil monohydrate Form I.

In some embodiments, the concentration of Treprostinil in the basic Treprostinil aqueous solution may range from, but is not limited to, about 0.01 g/ml to about 0.10 g/ml, preferably about 0.02 g/ml to about 0.07 g/ml, and more preferably about 0.03 g/ml to about 0.05 g/ml. The basic Treprostinil aqueous solution can be prepared at a temperature ranging from about 0° C. to about 60° C., preferably from about 10° C. to about 50° C., and more preferably from room temperature to about 40° C., but the disclosure is not limited thereto.

In some embodiments, the phosphoric acid may be prepared in the form of a phosphoric acid aqueous solution. In some embodiments, the phosphoric acid aqueous solution added to the basic Treprostinil aqueous solution is prepared by adding phosphoric acid to water. The concentration of the phosphoric acid aqueous solution may range from, but is not limited to, about 0.1 N to about 20 N, preferably about 1 N to about 15 N, and more preferably about 5 N to about 10 N, but the disclosure is not limited thereto. In some embodiments, the pH value of the Treprostinil aqueous solution is adjusted, but not limited to, about 2 to about 6, preferably about 2 to about 5, and more preferably about 2 to about 4 by adding the phosphoric acid aqueous solution. The phosphoric acid aqueous solution can be added to the basic Treprostinil aqueous solution at a temperature ranging from about 0° C. to about 60° C., preferably from about 10° C. to about 50° C. and more preferably from rom temperature to about 40° C., but the disclosure is not limited thereto. The decreasing rate of the pH value of the Treprostinil aqueous solution should be controlled to less than about 0.2 per minute. The lower limit of the decreasing rate of the pH value of the Treprostinil aqueous solution is not limited herein, and may be any suitable value as pre-determined or determined. In some embodiments, the phosphoric acid aqueous solution is added to the basic Treprostinil aqueous solution for more than about 30 minutes.

In some embodiments, the precipitation of the crystalline Treprostinil monohydrate Form I may be performed at a temperature ranging from about 0° C. to about 60° C., preferably from about 5° C. to about 50° C., and more preferably from 10° C. to about 40° C., but the disclosure is not limited thereto.

In some embodiments, the step of filtering out the precipitate comprises using water to wash the precipitate. The volume of the washing water may be about 50 ml to about 400 ml, preferably about 75 ml to about 350 ml, and more preferably about 100 ml to about 300 ml, per 1 g of the precipitate, but the disclosure is not limited thereto. As a result of not using an organic solvent, the obtained Treprostinil monohydrate Form I crystal does not contain any residual organic solvent. The Treprostinil monohydrate Form I crystal without residual organic solvent is very easily filtered compared with the slurry specimen as disclosed by U.S. Pat. No. 9,822,057 and U.S. Ser. No. 10/167,247 or the gummy solid or sticky liquid as prepared by WO 2009/137066 and *J. Org. Chem.* 69, 1890-1902 (2004). The filtered Treprostinil monohydrate Form I crystal has low viscosity and can be easily peeled from the bucket and dried due to its compact solid feature.

In some embodiments, the step of drying the Treprostinil monohydrate Form I crystal can be performed under reduced pressure of about 0.001 Torr to about 20 Torr, preferably about 0.01 Torr to about 10 Torr, and more preferably about 0.01 torr to about 1 torr, but the disclosure is not limited thereto. The drying step of the Treprostinil monohydrate Form I crystal can be performed at a temperature ranging from about 0° C. to about 40° C., preferably from about 5° C. to about 30° C., and more preferably from 10° C. to room temperature, but the disclosure is not limited thereto.

In comparison with the preparation processes of Treprostinil monohydrate (they take about four days with complex crushed steps) disclosed by U.S. Pat. No. 9,822,057 and U.S. Ser. No. 10/167,247, the method (it takes about four to six hours) provided by the present invention is much simpler and more time efficient. In addition, the method can drastically reduce the possibility of the formation of Treprostinil dimers and Treprostinil esterification impurities. Moreover, the Treprostinil monohydrate Form I crystal with granular characteristics obtained by the present invention is much easier to filter, dry, and be weighed for industrial handling.

Characterization of Crystalline Treprostinil Monohydrated Form I

Figure 7:
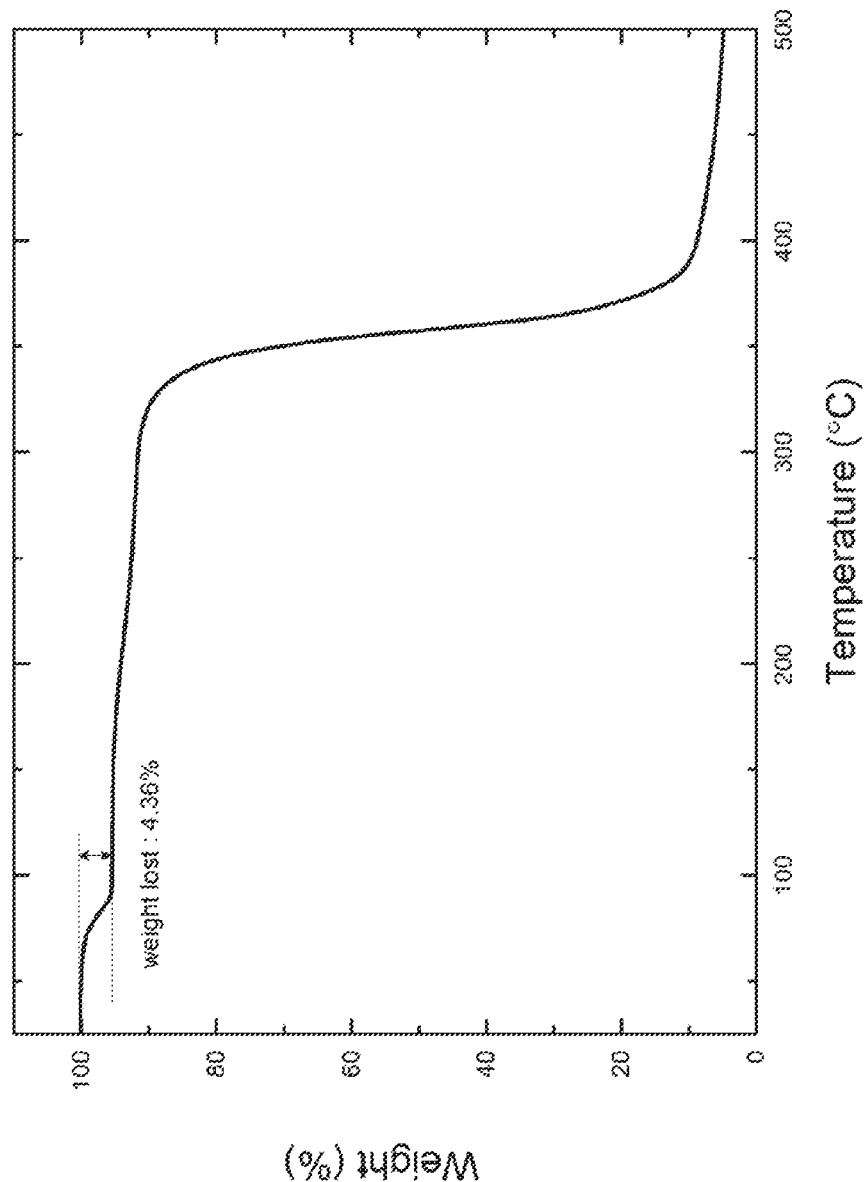
FIG. 7 shows a thermogravimetric analysis (TGA) pattern of the crystalline Treprostinil monohydrate Form I of the present invention.

The present invention provides novel crystalline Treprostinil monohydrate Form I. The characterization of the crystalline Treprostinil monohydrate Form I has been verified by Fourier transform infrared (FTIR) spectroscopy, Karl Fischer titration, and TGA. In one embodiment, the crystalline Treprostinil monohydrate Form I, exhibiting a characteristic FTIR peak at around $3513\pm4$ $cm^{-1}$, emphasizes the feature of hydrates, which indicates that the hydrated form of Treprostinil is a distinct molecular entity. Moreover, one mole of water molecules in Treprostinil calculates to 4.41% by weight. The content of about $4.41\pm1\%$ water measured by Karl Fischer titration and TGA (as shown in FIG. 7) confirms that there is one mole of water present in the hydrated form of Treprostinil. The crystalline Treprostinil monohydrate Form I obtained by the method of the present invention is essentially a monohydrated form. The crystalline Treprostinil monohydrate Form I has a purity of at least 99.5%, at least 99.6%, at least 99.7%, at least 99.8%, or at least 99.9%, aside from residual solvents.

In one embodiment, the crystalline Treprostinil monohydrate Form I has an XRPD pattern exhibiting its two strongest characteristic peaks at the following 2θ reflection angles: $5.43\pm0.2°$, and $10.87\pm0.2°$. In some embodiments, the XRPD pattern is substantially free of a characteristic peak at 2θ reflection angle of 21.71° (the strongest peak of Form A) or 21.56° (the strongest peak of Form B). In a preferred embodiment, the XRPD pattern further comprises characteristic peaks at the following 2θ reflection angles: $12.30\pm0.2°$, $16.34\pm0.2°$, and $20.39\pm0.2°$. More preferably, the XRPD pattern of crystalline Treprostinil monohydrate Form I is consistent with FIG. 5. The particular data of crystalline Treprostinil monohydrate Form I is shown in Table 1.

TABLE 1

| 2θ angle (°) | d value (Å) | relative intensity (%) |
|---|---|---|
| 5.43 | 16.262 | 94 |
| 6.05 | 14.597 | 23 |
| 6.61 | 13.361 | 12 |
| 8.21 | 10.761 | 5 |
| 10.87 | 8.133 | 100 |
| 12.30 | 7.190 | 40 |
| 13.19 | 6.707 | 31 |
| 16.34 | 5.420 | 49 |
| 17.41 | 5.090 | 6 |
| 18.81 | 4.714 | 14 |
| 19.65 | 4.514 | 13 |
| 20.39 | 4.352 | 53 |
| 20.74 | 4.279 | 21 |
| 21.32 | 4.164 | 22 |
| 21.66 | 4.087 | 42 |
| 22.42 | 3.962 | 24 |
| 23.26 | 3.821 | 13 |
| 24.05 | 3.697 | 7 |
| 24.61 | 3.614 | 24 |
| 25.43 | 3.500 | 9 |
| 26.26 | 3.391 | 8 |
| 27.05 | 3.294 | 8 |
| 28.71 | 3.107 | 7 |
| 29.24 | 3.052 | 5 |
| 30.34 | 2.944 | 5 |
| 31.39 | 2.848 | 5 |
| 32.26 | 2.773 | 4 |
| 33.42 | 2.679 | 4 |
| 36.94 | 2.431 | 4 |
| 37.71 | 2.384 | 4 |

Figure 5:
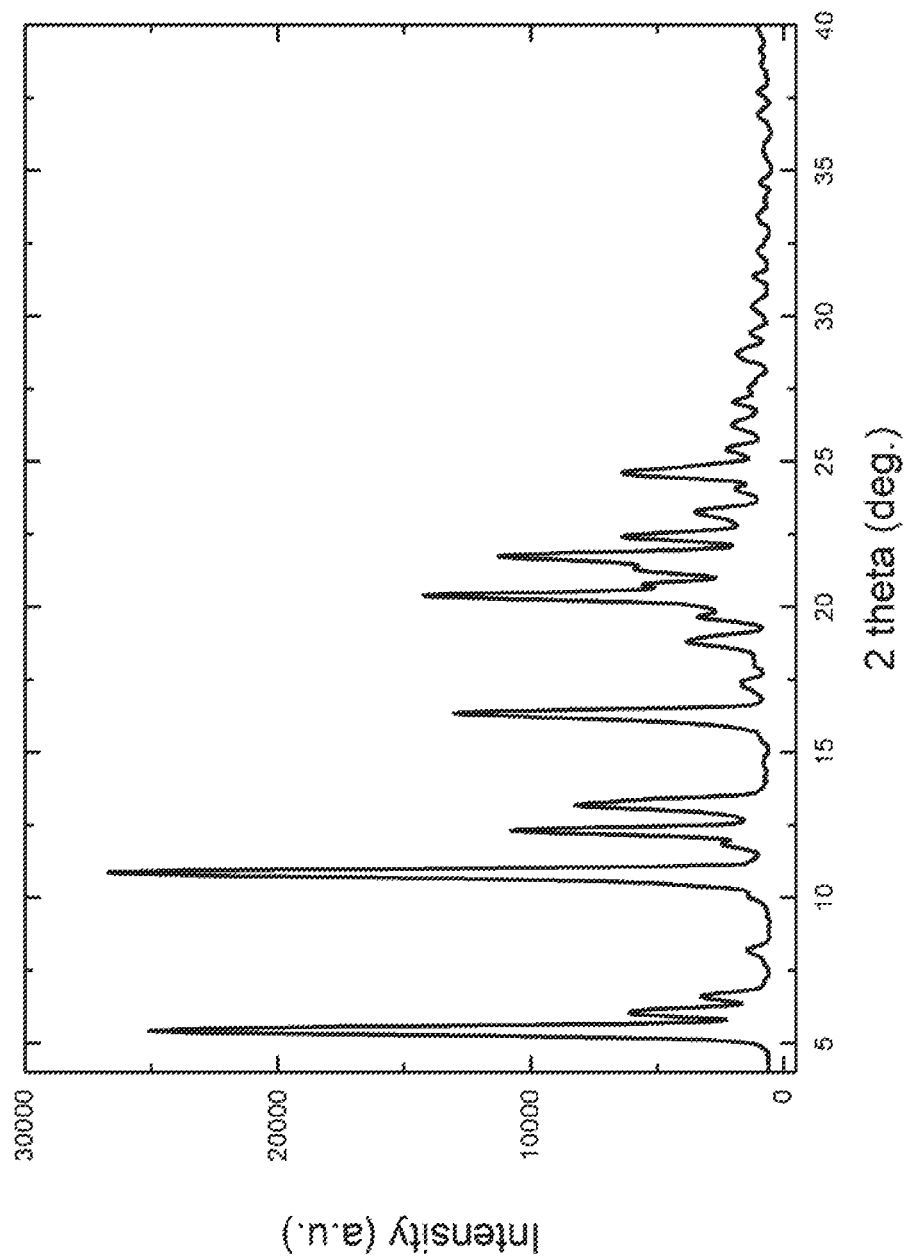
FIG. 5 shows an X-ray power diffraction (XRPD) pattern of the crystalline Treprostinil monohydrate Form I of the present invention.

In one embodiment, the present invention provides a crystalline Treprostinil monohydrate Form I having an XRPD pattern substantially as shown in FIG. 5.

The crystalline Treprostinil monohydrate Form I is different from the crystalline Treprostinil monohydrate Form A or Form B disclosed by U.S. Pat. No. 9,822,057 and U.S. Ser. No. 10/167,247 according to the XRPD features. The two strongest characteristic peaks of Form I are located at 5.43° and 10.87°, which are obviously different as compared with the two strongest characteristic peaks at 10.36° and 21.71 for Form A and at 20.56° and 21.56° for Form B. The crystalline Treprostinil monohydrate Form I does not have a strongest characteristic peak at 21.71° or 21.56°, which means that Form I is substantially free of Form A and Form B. In the present invention, the crystalline Treprostinil monohydrate Form I is substantially free of a characteristic peak at 2θ reflection of 21.71° or 21.56°. When used herein, the term "substantially free of a characteristic peak" means that in the XRPD pattern of the crystalline Treprostinil monohydrate Form I, the peak intensity at 21.71° or 21.56° is less than 10%, and preferably less than 3% of the strongest peak intensity at $10.87\pm0.2°$. In addition, Form A comprises two peaks at 5.17° and 5.88° in the range of 5 to 7°, but Form I comprises three different peaks at 5.43°, 6.05°, and 6.61° within the range of 5 to 70. Form A further comprises four peaks at 10.36°, 11.62°, 12.59°, and 13.15° in the range of 10 to 14°, but Form I comprises three different peaks at 10.87°, 12.30°, and 13.19° within the range of 10 to 14°. However, Form B comprises four peaks at 10.66°, 12.10°, 12.90°, and 13.10° in the range of 10 to 14°, but Form I comprises three different peaks at 10.87°, 12.30°, and 13.19° within the range of 10 to 14°. Form B further comprises ten peaks at 19.45°, 19.80°, 20.17°, 20.56°, 20.99°, 21.22°, 21.56°, 22.26°, 22.91°, and 23.10° in the range of 19 to 23.5°, but Form I comprises seven different peaks at 19.65°, 20.39°, 20.74°, 21.32°, 21.66°, 22.42°, and 23.26° with an obvious (and relative) intensity difference within said range. In addition, peaks at 10.36° belonging to Form A and 10.66° belonging to Form B do not exist in the XRPD pattern of Form I, indicating that Form I is an independent crystalline form without comprising Form A and/or Form B, and that Form I is different from Form A or Form B. Based on the differences in position and relative intensity from XRPD peaks as compared with the crystalline Treprostinil monohydrate Form A and Form B, although the invention is not limited by any theory, it is believed that the peak differences result from the structural differences, rather than from sample conditions such as particle size. This confirms that the crystalline Treprostinil monohydrate Form I is a novel crystalline form.

Figure 6:
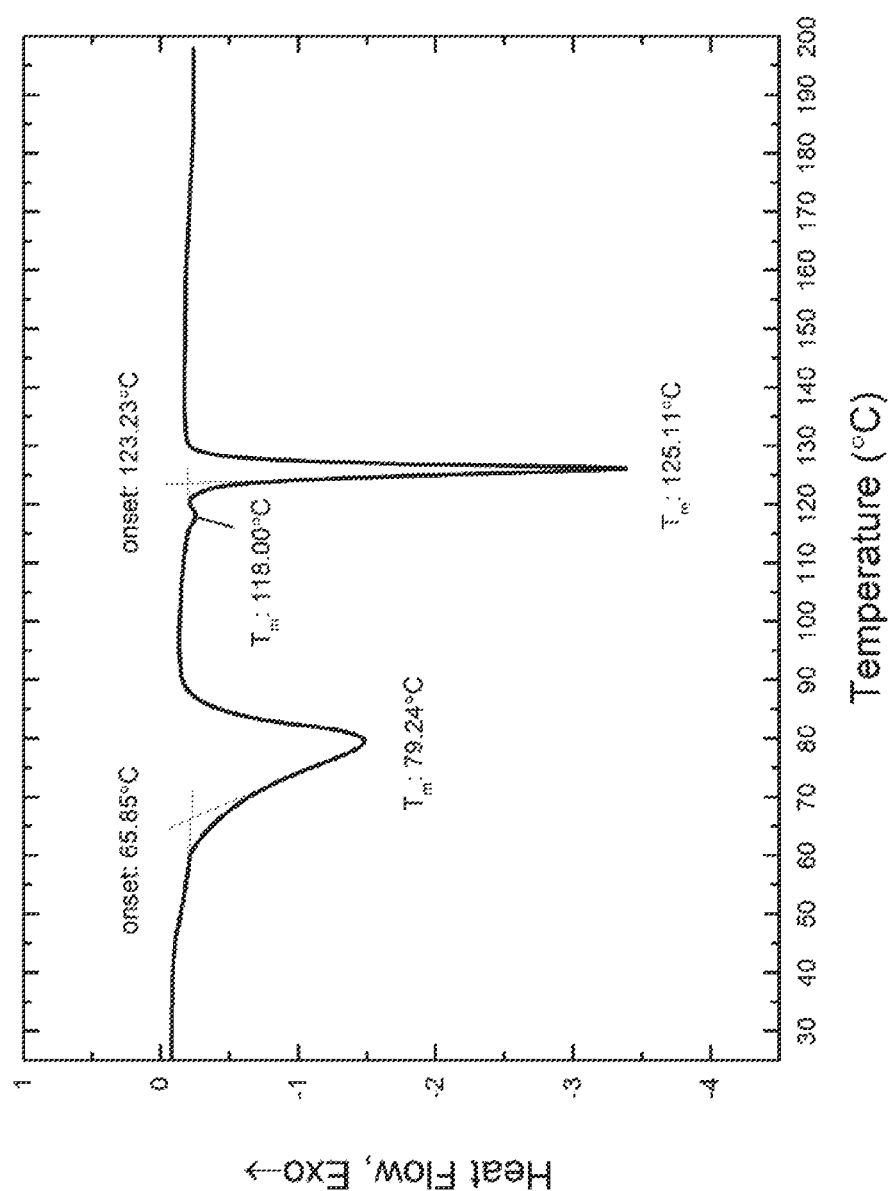
FIG. 6 shows a differential scanning calorimetry (DSC) thermogram pattern of the crystalline Treprostinil monohydrate Form I of the present invention.

In one embodiment, the present invention provides a crystalline Treprostinil monohydrate Form I having a differential scanning calorimetry (DSC) thermogram pattern comprising two major endothermic peaks, one with a peak onset temperature of 65.9±2° C. and a peak maximum of 79.2±2° C. and the other with a peak onset temperature of 123.2±2° C. and a peak maximum of 125.1±2° C. In a preferred embodiment, the present invention provides a crystalline Treprostinil monohydrate Form I having a DSC thermogram pattern substantially as shown in FIG. 6.

Figure 2:
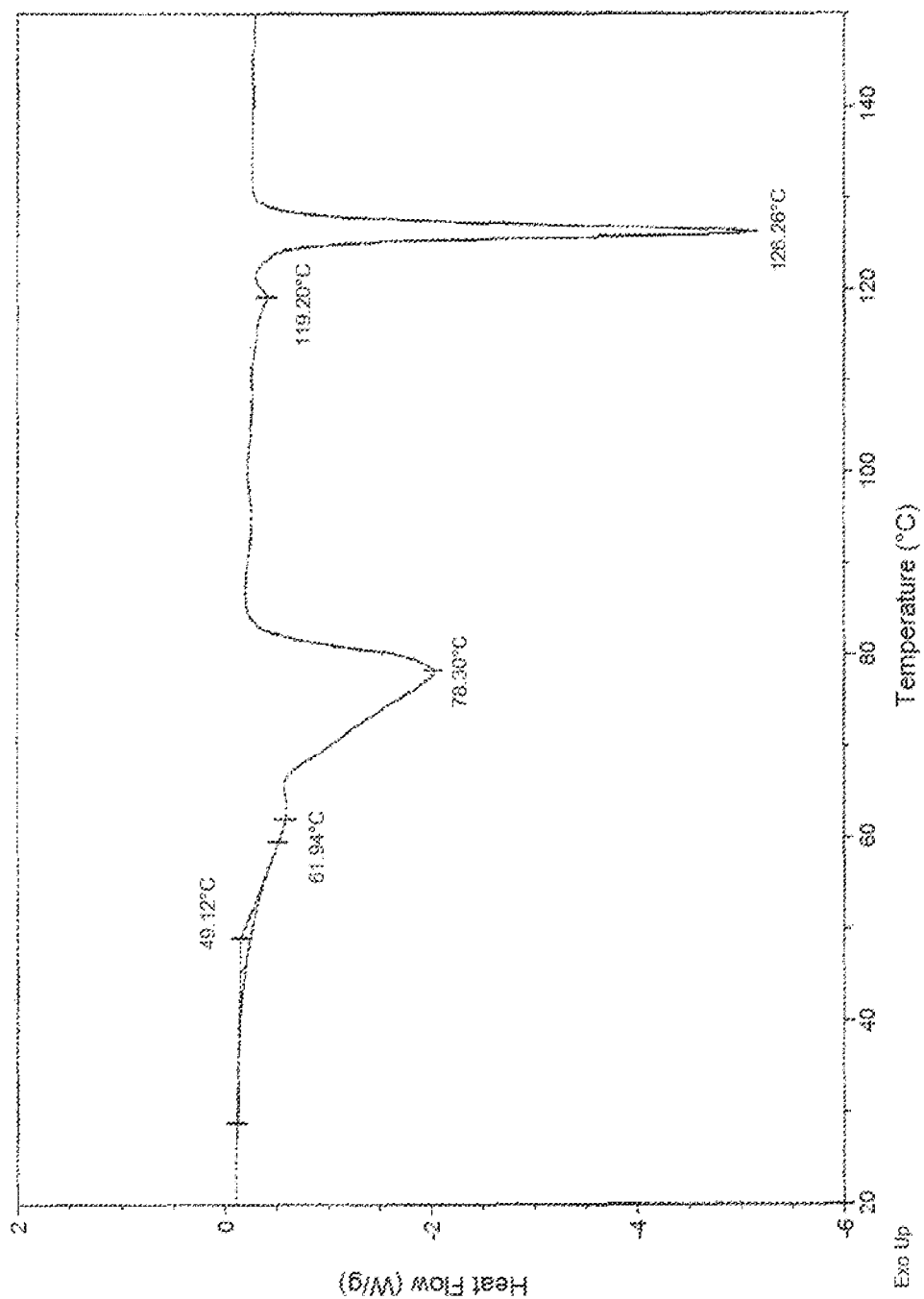
FIG. 2 shows a differential scanning calorimetry (DSC) thermogram pattern of the crystalline Treprostinil monohydrate Form A.
Figure 3:
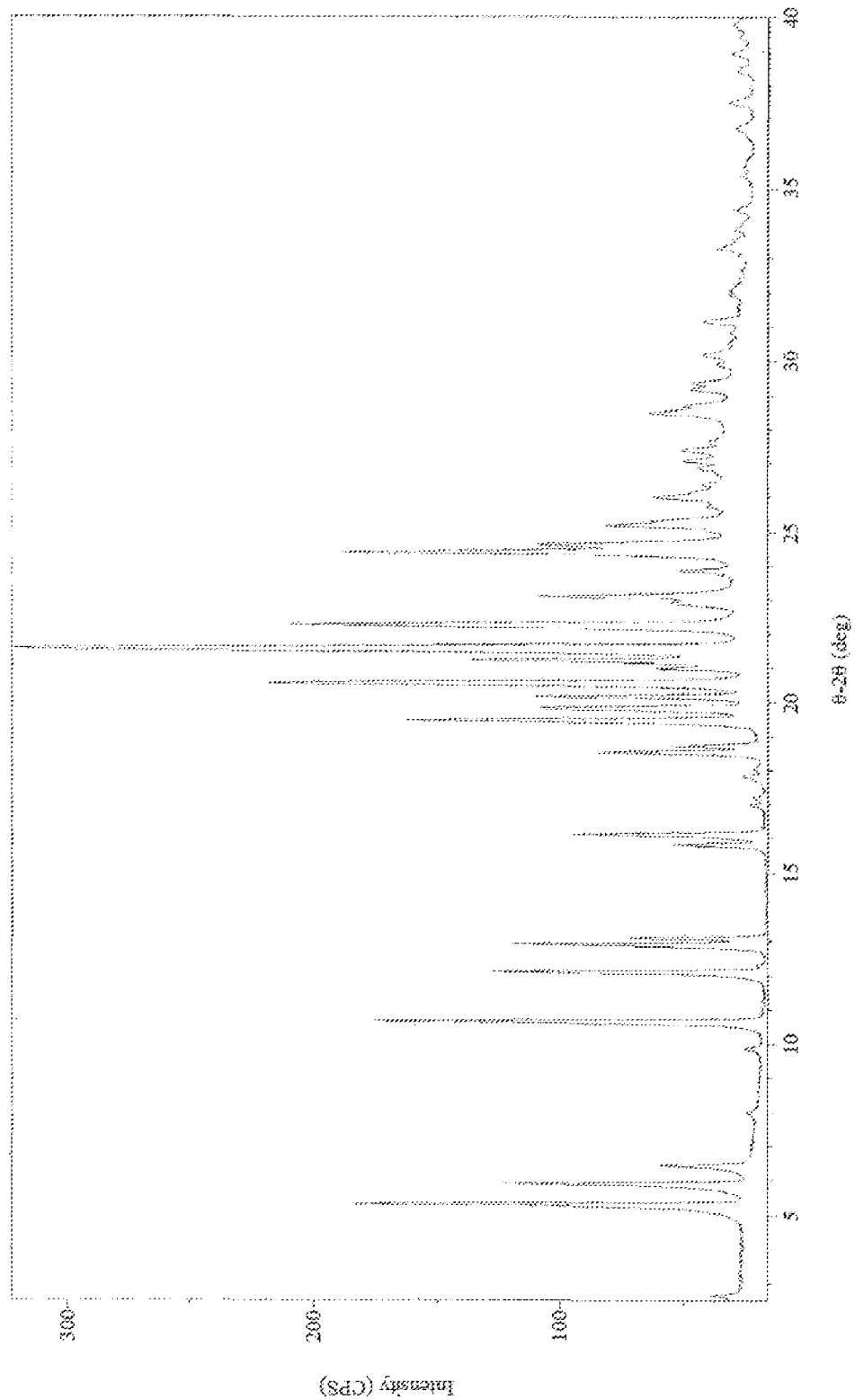
FIG. 3 shows an X-ray power diffraction (XRPD) pattern of the crystalline Treprostinil monohydrate Form B.
Figure 4:
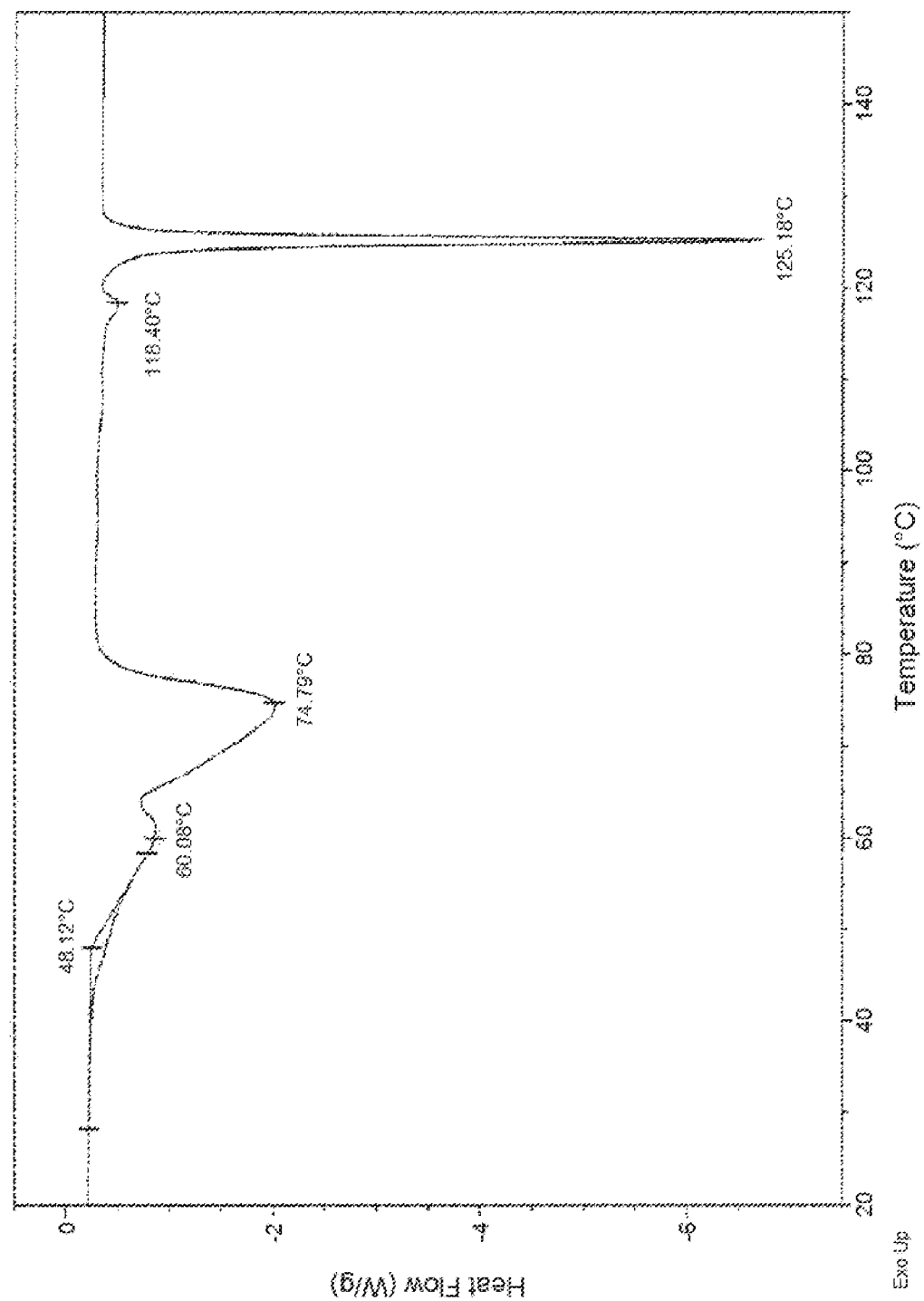
FIG. 4 shows a differential scanning calorimetry (DSC) thermogram pattern of the crystalline Treprostinil monohydrate Form B.

In one embodiment, the DSC feature of the crystalline Treprostinil monohydrate Form I is different as compared with the crystalline Treprostinil monohydrate Form A (FIG. 2) and Form B (FIG. 4) disclosed by U.S. Pat. No. 9,822,057 and U.S. Ser. No. 10/167,247. Form A comprises two peaks at around 61.94° C. and 78.30° C., and a peak at around 126.26° C. and Form B comprises two peaks at around 60.08° C. and 74.79° C., and a peak at around 125.18° C. However, Form I only comprises a peak at about 79.24° C. and a peak at about 125.11° C. The onset temperature (65.85° C.) of the 79.24° C. peak for Form I is higher than the peak maximum temperature of the 61.94° C. peak for Form A and 60.08° C. peak for Form B, indicating that the crystalline Treprostinil monohydrate Form I lacks 61.94° C. and 60.08° C. peaks. The features of different temperatures of the peak at about 79.24° C. and the disappearance of the peak at around 60.08° C. to 61.94° C. indicate that the crystalline Treprostinil monohydrate Form I comprises a unique crystalline form as compared with the crystalline Treprostinil monohydrate Form A and Form B, and that Form I is different from Form A or Form B. In some embodiments, the crystalline Treprostinil monohydrate Form I is substantially free of any other form of crystalline Treprostinil.

In one embodiment, the Treprostinil monohydrate Form I crystal has much better filterability due to its crystal characteristic as compared with the slurry specimen of crystalline Treprostinil monohydrate Form A and Form B as disclosed by U.S. Pat. No. 9,822,057 and U.S. Ser. No. 10/167,247, or the gummy solid or sticky liquid of crystalline Treprostinil monohydrate as prepared by WO 2009/137066 and J. Org. Chem. 69, 1890-1902 (2004). The benefits of the Treprostinil monohydrate Form I crystal with good filterability are that: (1) the unwanted impurities dissolved in the filtrate can be easily removed while filtering and rinsing the Treprostinil monohydrate Form I crystal, (2) the impurities raised from residual solvent can be avoided since the filtering time for Treprostinil monohydrate Form I crystal is short, and (3) the filtered Treprostinil monohydrate Form I crystal can be dried easily. Based on the above advantages, the esterification impurities of Treprostinil can be easily eliminated and the formation of Treprostinil dimers can be prevented.

Crystalline Treprostinil Monohydrate Form II and Preparation Thereof

In an embodiment, the method for preparing crystalline Treprostinil monohydrate Form II or the Treprostinil monohydrate Form II crystal comprises the steps of:
(a) providing a basic Treprostinil aqueous solution;
(b) quickly adding phosphoric acid to the basic Treprostinil aqueous solution until the aqueous solution becomes acidic, having a pH value of about 2 to about 4, wherein the pH value of the aqueous solution is decreased at a rate of more than about 0.6 per minute;
(c) stirring until a precipitate is formed;
(d) filtering out the precipitate and/or adding water for rinsing the precipitate, thereby isolating the crystalline Treprostinil monohydrate Form II; and
(e) optionally drying the crystalline Treprostinil monohydrate Form II.

In some embodiments, the concentration of Treprostinil in the basic Treprostinil aqueous solution may range from, but is not limited to, about 0.01 g/ml to about 0.10 g/ml, preferably about 0.02 g/ml to about 0.07 g/ml, and more preferably about 0.03 g/ml to about 0.05 g/ml. The basic Treprostinil aqueous solution can be prepared at a temperature ranging from about 0° C. to about 60° C., preferably from about 10° C. to about 50° C., and more preferably from room temperature to about 40° C., but the disclosure is not limited thereto.

In some embodiments, the phosphoric acid may be prepared in the form of a phosphoric acid aqueous solution. In some embodiments, the phosphoric acid aqueous solution added to the basic Treprostinil aqueous solution is prepared by adding phosphoric acid to water. The concentration of the phosphoric acid aqueous solution may range from, but is not limited to, about 0.1 N to about 20 N, preferably about 1 N to about 15 N, and more preferably about 5 N to about 10 N, but the disclosure is not limited thereto. In some embodiments, the pH value of the Treprostinil aqueous solution is adjusted, but not limited to, about 2 to about 6, preferably about 2 to about 5, and more preferably about 2 to about 4 by adding the phosphoric acid aqueous solution. The phosphoric acid aqueous solution can be added to the basic Treprostinil aqueous solution at a temperature ranging from about 0° C. to about 60° C. preferably from about 10° C. to about 50° C., and more preferably from room temperature to about 40° C., but the disclosure is not limited thereto. The decreasing rate of the pH value of the Treprostinil aqueous solution should be controlled to more than about 0.6 per minute. The upper limit of the decreasing rate of the pH value of the Treprostinil aqueous solution is not limited herein, and may be any suitable value as pre-determined or determined. In some embodiments, the phosphoric acid aqueous solution is added to the basic Treprostinil aqueous solution within about 1 to about 10 minutes.

In some embodiments, the precipitation of the Treprostinil monohydrate Form II crystal may be performed at a temperature ranging from about 0° C. to about 60° C., preferably from about 5° C. to about 50° C., and more preferably from 10° C. to about 40° C., but the disclosure is not limited thereto.

In some embodiments, the step of filtering out the precipitate comprises using the water to wash the precipitate. The volume of the washing water may be about 50 ml to about 400 ml, preferably about 75 ml to about 350 ml, and more preferably about 100 ml to about 300 ml, per 1 g of the precipitate, but the disclosure is not limited thereto. As a result of not using an organic solvent, the obtained Treprostinil monohydrate Form II crystal does not contain any residual organic solvent. The Treprostinil monohydrate Form II crystal without residual organic solvent is very easily filtered as compared with the slurry specimen as disclosed by U.S. Pat. No. 9,822,057 and U.S. Ser. No. 10/167,247, and the gummy solid or sticky liquid as prepared by WO 2009/137066 and *J. Org. Chem.* 69, 1890-1902 (2004). The filtered Treprostinil monohydrate Form II crystal has low viscosity and can be easily peeled from the bucket and dried due to its compact solid feature.

In some embodiments, the step of drying the Treprostinil monohydrate Form II crystal can be performed under reduced pressure of about 0.001 Torr to about 20 Torr, preferably about 0.01 Torr to about 10 Torr, and more preferably about 0.01 torr to about 1 torr, but the disclosure is not limited thereto. The drying step of the Treprostinil monohydrate Form II crystal can be performed at a temperature ranging from about 0° C. to about 40° C., preferably from about 5° C. to about 30° C. and more preferably from 10° C. to room temperature, but the disclosure is not limited thereto.

In comparison with the preparation processes of Treprostinil monohydrate (they take about four days with complex crushed steps) disclosed by U.S. Pat. No. 9,822,057 and U.S. Ser. No. 10/167,247, the novel method (it takes about four to six hours) provided by the present invention is much simpler and more time efficient. In addition, the method can drastically reduce the possibility of the formation of Treprostinil dimers and Treprostinil esterification impurities. Moreover, the Treprostinil monohydrate Form II crystal with granular characteristics obtained by present invention is much easier to filter, dry, and be weighed for industrial handling.

Characterization of Crystalline Treprostinil Monohydrated Form II

Figure 10:
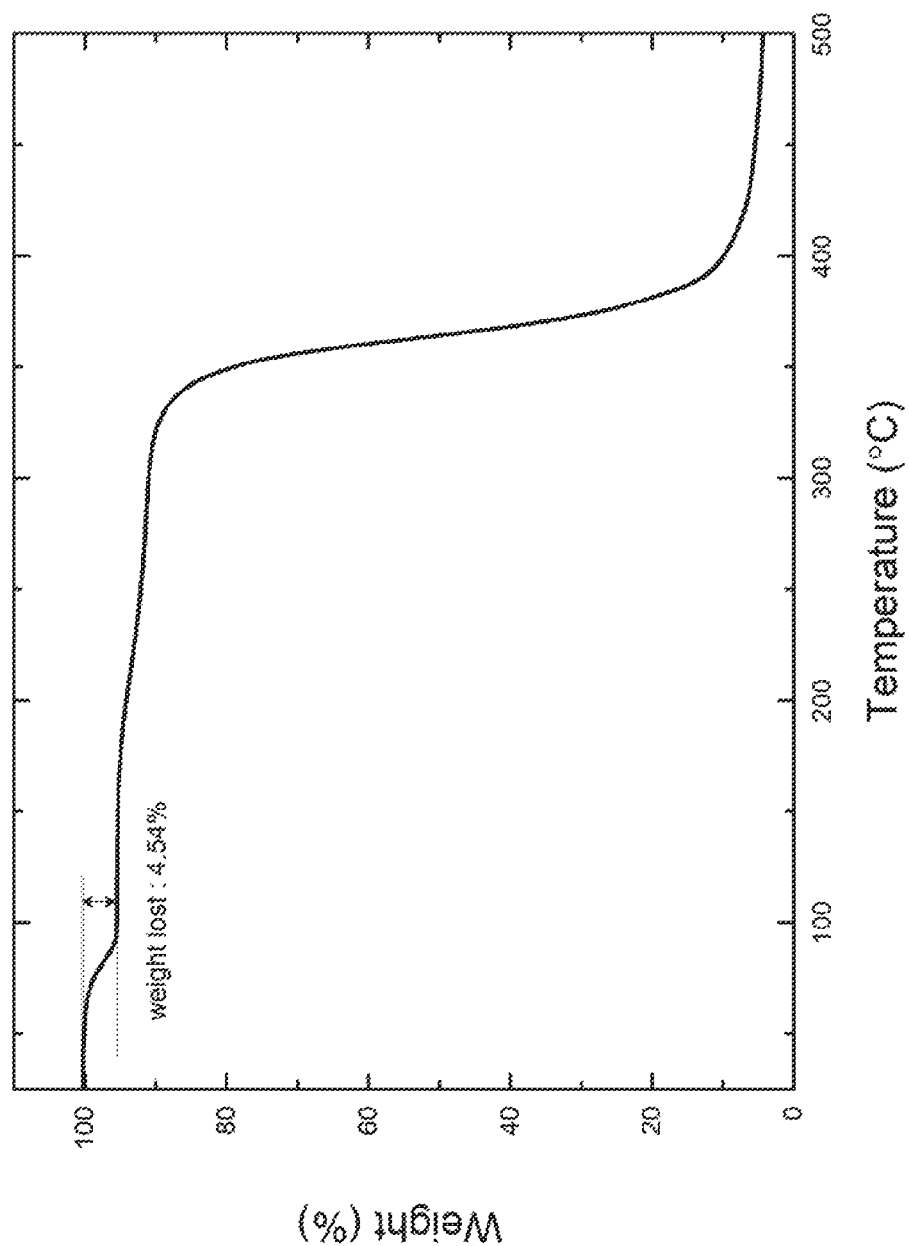
FIG. 10 shows a thermogravimetric analysis (TGA) pattern of the crystalline Treprostinil monohydrate Form II of the present invention.

The present invention also provides novel crystalline Treprostinil monohydrate Form II. The characterization of the crystalline Treprostinil monohydrate Form II has been verified by FTIR, spectroscopy, Karl Fischer titration, and TGA. In one embodiment, the crystalline Treprostinil monohydrate Form II, exhibiting a characteristic FTIR peak at around $3513\pm4$ cm$^{-1}$, emphasizes the feature of hydrates, which indicates that the hydrated form of Treprostinil is a distinct molecular entity. Moreover, one mole of water molecules in Treprostinil calculates to 4.41% by weight. In some embodiments, the content of about $4.41\pm1\%$ water measured by Karl Fischer titration and TGA (as shown in FIG. 10) confirms that there is one mole of water present in the hydrated form of Treprostinil. The crystalline Treprostinil monohydrate Form II obtained by the method of the present invention is essentially a monohydrated form. The crystalline Treprostinil monohydrate Form II has a purity of at least 99.5%, at least 99.6%, at least 99.7%, at least 99.8%, or at least 99.9%, aside from residual solvents.

In one embodiment, the crystalline Treprostinil monohydrate Form II has an XRPD pattern exhibiting its two strongest characteristic peaks at the following 2θ reflection angles: $5.19\pm0.2°$, and $10.40\pm0.2°$. In some embodiments, the XRPD pattern is substantially free of a characteristic peak at 2θ reflection of 21.71° (the strongest peak of Form A) or 21.56° (the strongest peak of Form B). In a preferred embodiment, the XRPD pattern further comprises characteristic peaks at the following 2θ reflection angles: $11.62\pm0.2°$, $16.19\pm0.2°$, and $20.14\pm0.2°$. More preferably, the XRPD pattern of crystalline Treprostinil monohydrate Form II is consistent with FIG. 8. The particular data of crystalline Treprostinil monohydrate Form II is shown in Table 2.

TABLE 2

| 2θ angle (°) | d value (Å) | relative intensity (%) |
|---|---|---|
| 5.19 | 17.013 | 73 |
| 5.93 | 14.892 | 3 |
| 7.64 | 11.562 | 2 |
| 8.10 | 10.907 | 3 |
| 10.40 | 8.499 | 100 |
| 11.62 | 7.609 | 23 |
| 12.61 | 7.014 | 8 |
| 13.16 | 6.707 | 8 |
| 15.27 | 5.798 | 3 |
| 15.58 | 5.683 | 7 |
| 16.19 | 5.470 | 30 |
| 16.99 | 5.214 | 2 |
| 18.22 | 4.865 | 4 |
| 18.81 | 4.714 | 3 |
| 20.14 | 4.399 | 44 |
| 20.82 | 4.263 | 5 |
| 21.13 | 4.201 | 8 |
| 21.29 | 4.170 | 6 |
| 21.69 | 4.094 | 2 |
| 22.71 | 3.912 | 1 |
| 23.77 | 3.740 | 2 |
| 24.40 | 3.645 | 2 |
| 26.11 | 6.410 | 5 |
| 28.32 | 3.149 | 2 |
| 32.38 | 2.763 | 2 |

Figure 8:
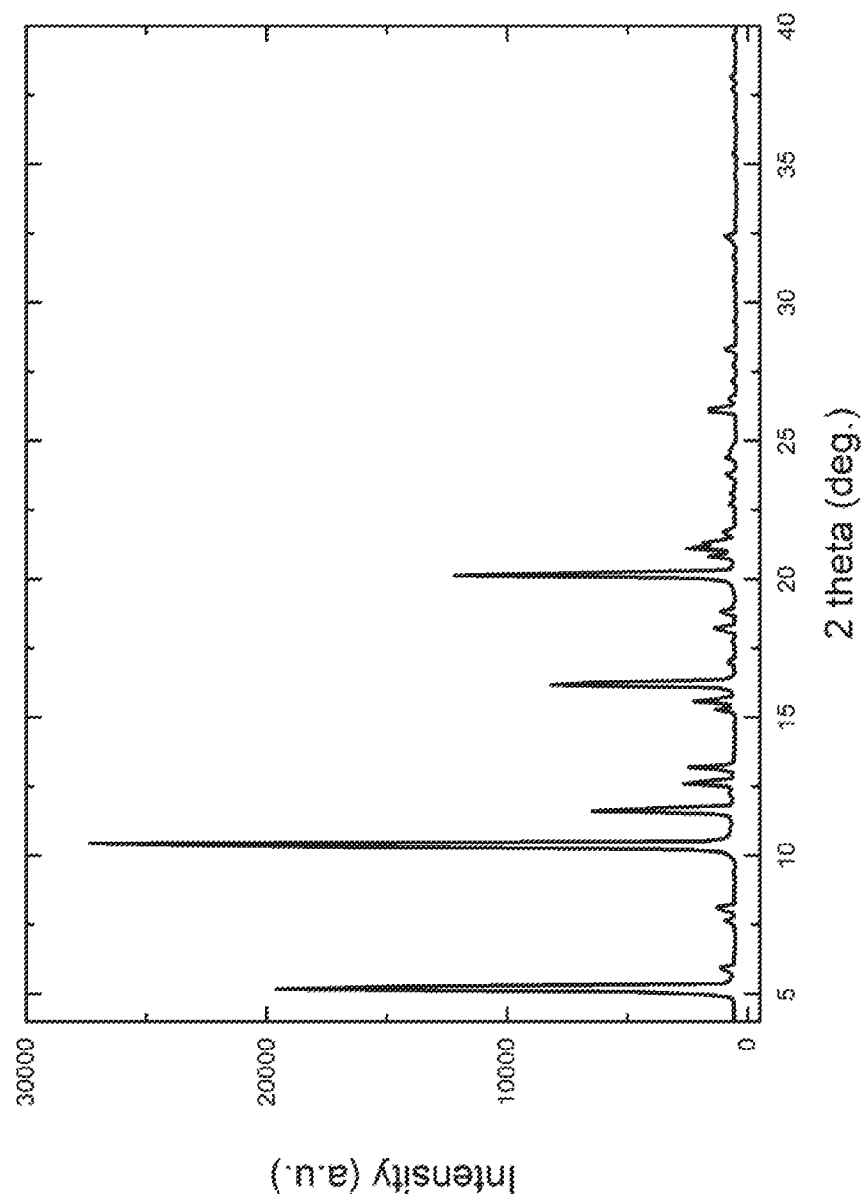
FIG. 8 shows an X-ray power diffraction (XRPD) pattern of the crystalline Treprostinil monohydrate Form II of the present invention.

In one embodiment, the present invention provides a crystalline Treprostinil monohydrate Form II having an XRPD pattern substantially as shown in FIG. 8.

The crystalline Treprostinil monohydrate Form II is different from the crystalline Treprostinil monohydrate Form A or Form B disclosed by U.S. Pat. No. 9,822,057 and U.S. Ser. No. 10/167,247 according to the XRPD features. The two strongest characteristic peaks of Form II are located at 5.2° and 10.4°, which are obviously different as compared with the two strongest characteristic peaks at 10.36° and 21.71° for Form A and at 20.56° and 21.56° for Form B. The crystalline Treprostinil monohydrate Form II is substantially free of a characteristic peak at 21.71° or 21.56°, which means that Form II is substantially free of Form A and Form B. When used herein, the term "substantially free of a characteristic peak" means that in the XRPD pattern of the crystalline Treprostinil monohydrate Form II, the peak intensity at 21.71° or 21.56° is less than 10%, preferably less than 3% of the strongest peak intensity at $10.40\pm0.2°$. In addition, Form II comprises five major peaks at 5.19°, 10.40°, 11.62°, 16.19°, and 20.14°; however, Form A comprises different five major peaks at 5.17°, 10.36°, 11.62°, 19.95°, and 21.71° within the range. Form A comprises seriously strong peaks in the range of 19 to 25°, but Form II comprises a major peak only at 20.14° within the range 19 to 25°. Notably. Form II comprises a peak at 21.13°, which is not present in the XRPD pattern of Form A. However, Form B comprises three peaks at 5.32°, 5.920, and 6.44° in the range of 5 to 7°, but Form II comprises only two peaks at 5.19° and 5.93° within the range of 5 to 7°. Form B further comprises four peaks at 10.66°, 12.10°. 12.90°, and 13.10° in the range of 10 to 14°, but Form II comprises four different peaks at 10.40°, 11.62°. 12.61°, and 13.19° within the range 10 to 14°. In addition, peaks at 23.06° belonged to Form A and 19.45° belonged to Form B do not exist in the XRPD pattern of Form II, indicating that Form II is an independent crystalline form without comprising Form A and/or Form B, and is different from Form A or Form B. Based on the differences of position and relative intensity from XRPD peaks comparing with the crystalline Treprostinil monohydrate Form A and Form B, although the invention is not limited by any theory, it is believed that the peak differences result from the structural differences instead of sample conditions such as particle size, which confirms that the crystalline Treprostinil monohydrate Form II is a novel crystalline form.

Figure 9:
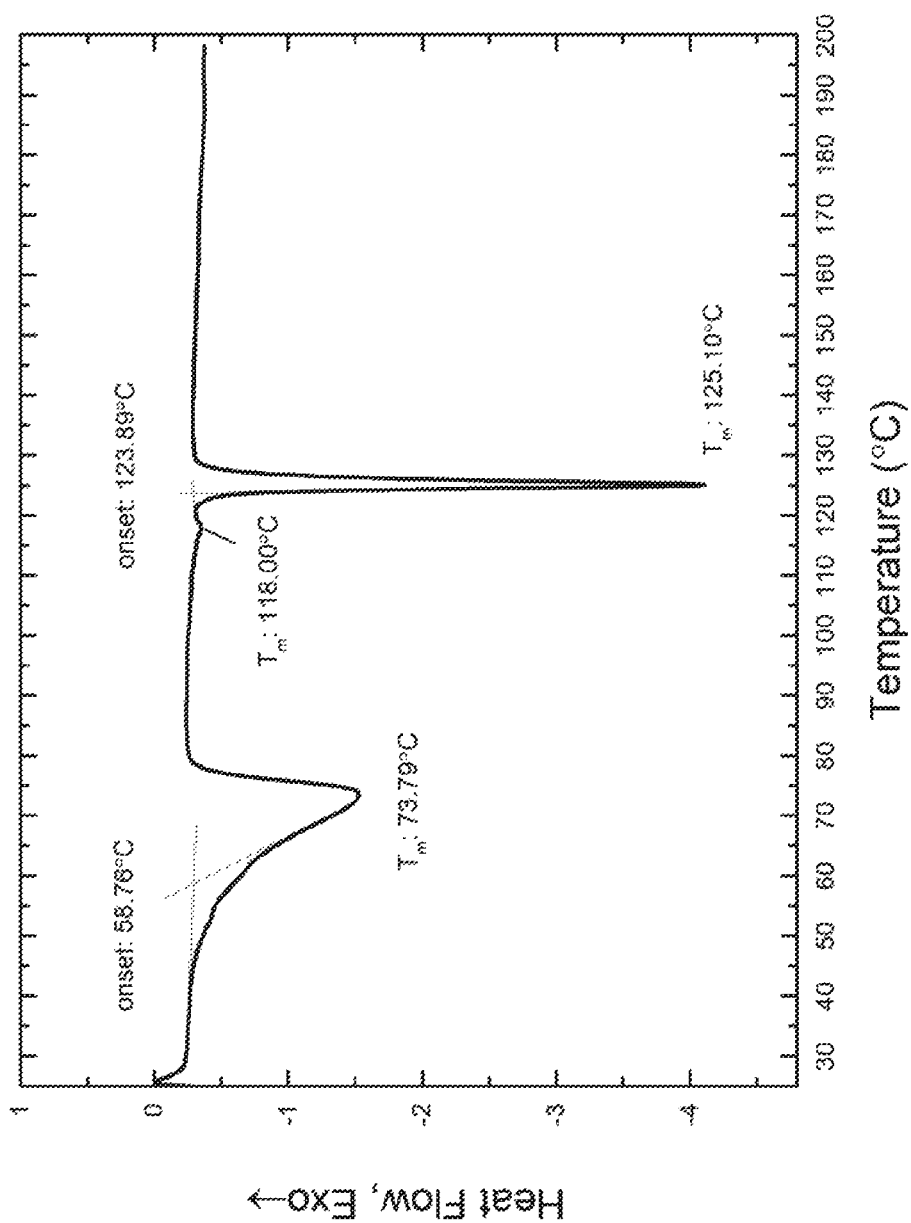
FIG. 9 shows a differential scanning calorimetry (DSC) thermogram pattern of the crystalline Treprostinil monohydrate Form II of the present invention.

In one embodiment, the present invention provides a crystalline Treprostinil monohydrate Form II having a DSC thermogram pattern comprising two major endothermic peaks, one with a peak onset temperature of 58.8±2° C. and a peak maximum of 73.8±2° C. and the other with a peak onset temperature of 123.9±2° C. and a peak maximum of 125.1±2° C. In a preferred embodiment, the present invention provides a crystalline Treprostinil monohydrate Form II having a DSC thermogram pattern substantially as shown in FIG. 9.

In one embodiment, the DSC feature of the crystalline Treprostinil monohydrate Form II is different as compared to the crystalline Treprostinil monohydrate Form A (FIG. 2) and Form B (FIG. 4) disclosed by U.S. Pat. No. 9,822,057 and U.S. Ser. No. 10/167,247. Form A comprises two peaks at around 61.94° C. and 78.30° C. and a peak at around 126.26° C., and Form B comprises two peaks at around 60.08° C. and 74.79° C. and a peak at around 125.18° C. However, Form II comprises only a peak at about 73.79° C. and a peak at about 125.10° C. The onset temperature of 73.79° C. peak for Form II is 58.76° C. But the DSC thermogram pattern of Form II does not show a peak at 61.94° C. or 60.08° C., indicating that the crystalline Treprostinil monohydrate of Form II lacks 61.94° C. peak for Form A and 60.08° C. peak for Form B. The features of different temperatures of the peak at about 73.8° C. and the disappearance of the peak at around 60.08° C. to 61.94° C. indicates that the crystalline Treprostinil monohydrate Form II comprises unique a crystalline form as compared with the crystalline Treprostinil monohydrate Form A and Form B, and is different from Form A or Form B. In some embodiments, the crystalline Treprostinil monohydrate Form II is substantially free of any other form of crystalline Treprostinil.

In one embodiment, the Treprostinil monohydrate Form II crystal has much better filterability due to its crystal characteristic as compared with the slurry specimen of crystalline Treprostinil monohydrate Form A and Form B as disclosed by U.S. Pat. No. 9,822,057 and U.S. Ser. No. 10/167,247, or the gummy solid or sticky liquid of crystalline Treprostinil monohydrate as prepared by WO 2009/137066 and *J. Org. Chem.* 69, 1890-1902 (2004). The benefits of the Treprostinil monohydrate Form II crystal with good filterability are that (1) the unwanted impurities dissolved in the filtrate can be easily removed while filtering and rinsing the Treprostinil monohydrate Form II crystal, (2) the impurities raised from residual solvent can be avoided since the filtering time of Treprostinil monohydrate Form II crystal is short, and (3) the filtered Treprostinil monohydrate Form II crystal is easily dried. Based on above advantages, the esterification impurities of Treprostinil can be easily eliminated and the formation of Treprostinil dimers can be prevented.

Figure 11:
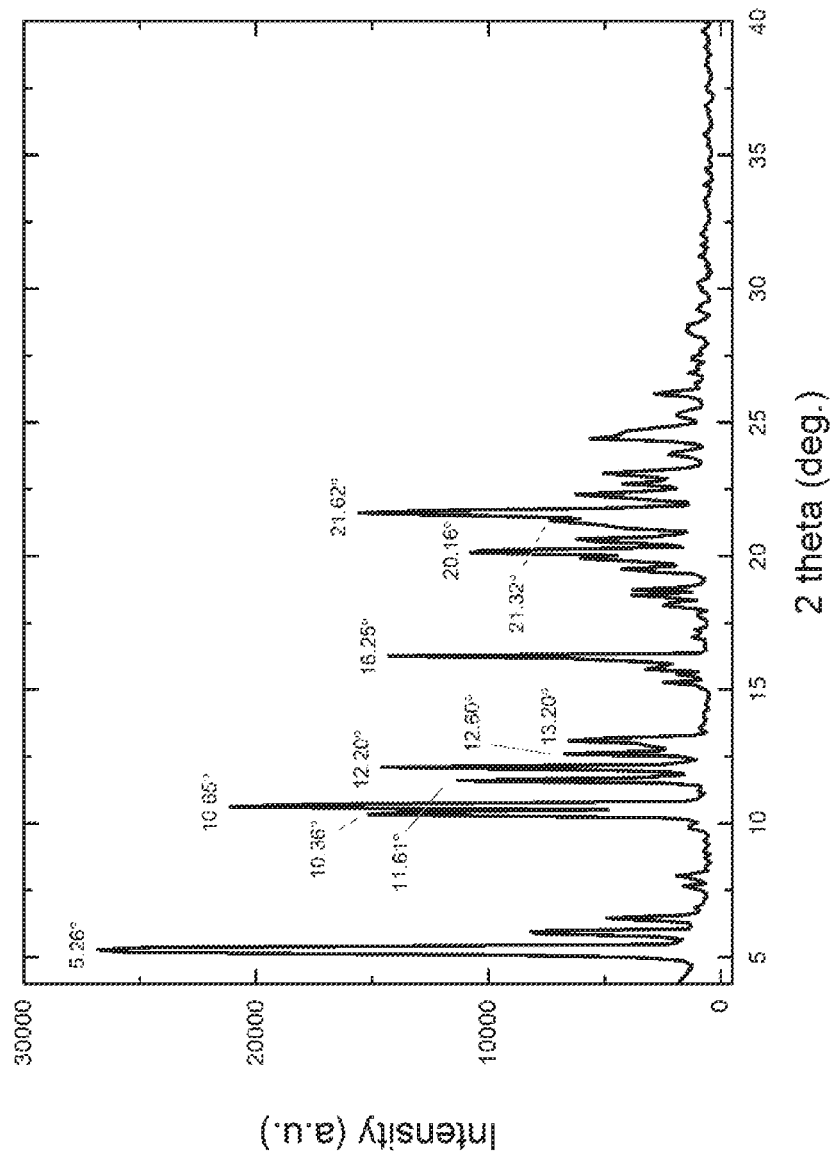
FIG. 11 shows an X-ray power diffraction (XRPD) pattern of the mixture of crystalline Treprostinil monohydrate Form I and crystalline Treprostinil monohydrate Form II of the present invention.

Preparation of the Mixture of Treprostinil Monohydrate Form I and Form II Crystals In the present invention, the decreasing rate of pH value adjusted by adding phosphoric acid during preparation of the Treprostinil monohydrate crystal is the key to determining whether a crystalline Treprostinil monohydrate Form I or Form II can be obtained. When the decreasing rate of pH value is controlled to more than about 0.6 per minute, Form II is preferentially precipitated. However. Form I is preferentially precipitated when the decreasing rate of pH value is controlled to less than about 0.2 per minute. The mixture of Treprostinil monohydrate Form I and Form II crystals can be obtained when the decreasing rate of pH value is controlled between about 0.2 and about 0.6 per minute. The other operation conditions for preparing the mixture of Treprostinil monohydrate Form I and Form II crystals are similar to those for preparing Form I or Form II, and thus are omitted. The preparation method for the mixture of Treprostinil monohydrate Form I and Form II crystals is shown in Example 7, and the resulting XRPD pattern is shown in FIG. 11. The particular data of the mixture of Treprostinil monohydrate Form I and Form II crystals is shown in Table 3.

TABLE 3

| 2θ angle (°) | d value (Å) | relative intensity (%) |
|---|---|---|
| 5.26 | 16.787 | 100 |
| 5.92 | 14.917 | 33 |
| 6.55 | 13.484 | 18 |
| 7.63 | 11.577 | 6 |
| 8.13 | 10.866 | 7 |
| 10.36 | 8.532 | 61 |
| 10.65 | 8.300 | 82 |
| 11.61 | 7.616 | 42 |
| 12.20 | 7.249 | 55 |
| 12.60 | 7.020 | 25 |
| 13.20 | 6.702 | 24 |
| 15.27 | 5.798 | 9 |
| 15.57 | 5.687 | 7 |
| 15.79 | 5.608 | 12 |
| 16.25 | 5.450 | 54 |
| 16.97 | 5.221 | 5 |
| 18.18 | 4.876 | 10 |
| 18.53 | 4.784 | 14 |
| 18.74 | 4.731 | 14 |
| 19.61 | 4.523 | 16 |
| 19.93 | 4.451 | 22 |
| 20.16 | 4.401 | 42 |
| 20.60 | 4.308 | 24 |
| 21.32 | 4.164 | 27 |
| 21.62 | 4.107 | 58 |
| 22.29 | 3.985 | 23 |
| 22.71 | 3.912 | 16 |
| 23.09 | 3.849 | 19 |
| 23.81 | 3.734 | 8 |
| 24.41 | 3.644 | 22 |
| 25.29 | 3.519 | 7 |
| 26.08 | 3.414 | 11 |

In some embodiments, the mixture of crystalline Treprostinil monohydrate Form I and crystalline Treprostinil monohydrate Form II has an XRPD pattern comprising its jointly characteristic peaks at 5.26±0.2°, 13.20±0.2°, and 16.25±0.2° for Form I and Form II, and its separated characteristic peaks at 10.65±0.2° and 12.20±0.2° belonging to Form I and at 10.36±0.2°, 11.61±0.2°, and 12.60±0.2° belonging to Form II. In one embodiment, peaks at 5.26±0.2°, 13.20±0.2°, and 16.25±0.2° are the jointly characteristic peaks for Form I and Form II resulting from the overlapping of nearby peaks for Form I at 5.43±0.2°. 13.20±0.2°, and 16.34±0.2° and peaks for Form II at 5.19±0.2°, 13.20±0.2°, and 16.19±0.2°. However, in the range of 10 to 14°, the appearance of separated characteristic peaks at 10.65°, and 12.20° are associated to Form I, and peaks at 10.36°. 11.61°, and 12.60° are associated to Form II, respectively. According to these results, it is believed that the specimen is a mixture of Treprostinil monohydrate Form I and Form II crystals. The lack of a strongest characteristic peak at 21.71° or 21.56° indicates that the mixture of Treprostinil monohydrate Form I and Form II crystals is substantially free of Treprostinil monohydrate Form A or Form B crystal. The mixture of Treprostinil monohydrate Form I and Form II crystals has a purity of at least 99.5%, at least 99.6%, at least 99.7%, at least 99.8%, or at least 99.9%, aside from residual solvents.

In some embodiments, the mixture of Treprostinil monohydrate Form I and Form II crystals comprises at least about 10% of Form I or Form II. In some embodiments, the mixture of Treprostinil monohydrate Form I and Form II crystals comprises from about 10% to 90% of Form I and about 90% to 10% of Form II, or from about 20% to 80% of Form I and about 80% to 20% of Form II, but the disclosure is not limited thereto. In some embodiments, the mixture of Treprostinil monohydrate Form I and Form II crystals is substantially free of any other form of crystalline Treprostinil.

In one embodiment, the mixture of Treprostinil monohydrate Form I and Form II crystals has much better filterability due to its crystal characteristic comparing with the slurry specimen of crystalline Treprostinil monohydrate Form A and Form B as disclosed by U.S. Pat. No. 9,822,057 and U.S. Ser. No. 10/167,247 or the gummy solid or sticky liquid of crystalline Treprostinil monohydrate as prepared by WO 2009/137066 and J. Org. Chen. 69, 1890-1902 (2004). The benefits of the mixture of Treprostinil monohydrate Form I and Form II crystals with good filterability are that (1) the unwanted impurities dissolved in the filtrate can be easily removed while filtering and rinsing the mixture of Treprostinil monohydrate Form I and Form II crystals, (2) the impurities raised from residual solvent can be avoided since the filtering time of the mixture of Treprostinil monohydrate Form I and Form II crystals is short, and (3) the filtered mixture of Treprostinil monohydrate Form I and Form II crystals can be dried easily. Based on above advantages, the esterification impurities of Treprostinil can be easily eliminated and the formation of Treprostinil dimers can be prevented.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 4° to 40° with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC thermogram patterns were collected on a TA DISCOVERY DSC25 instrument. The samples were weighed into an aluminum pan with a crimping closed aluminum lid. The prepared samples were analyzed from 25° C. to 200° C. at a scan rate of 10° C./min under a flow of nitrogen (ca. 50 ml/min). The melting temperature and heat of fusion were calibrated by indium (In) before measurement.

Thermogravimetric Analysis (TGA): The TGA thermogram patterns were collected on a TA Q500 instrument. The samples were weighed on a platinum pan. The prepared samples were analyzed from ambient temperature to 500° C. at a scan rate of 10° C./min under nitrogen. The temperature and weight calibration were both performed before measurement.

Ultra Performance Liquid Chromatography (UPLC) Analysis: The UPLC spectra were collected on a Waters ACQUITY UPLC instrument. The conditions were shown as the following: The sample is diluted to 1 mg/mi by 50/50 (v/v) acetonitrile/$H_2O$. The column is Waters BEH $C_{18}$, 1.7 μm, 2.1*150 mm. The mobile phase is 60/40 (v/v) buffer/acetonitrile from 0 to 10 min, gradient changes of buffer/acetonitrile from 60/40 to 5/95 (v/v) (curve 6) from 10 to 20 min, 5/95 (v/v) buffer/acetonitrile from 20 to 25 min, gradient changes of buffer/acetonitrile from 5/95 to 0/100 (v/v) (curve 6) from 25 to 30 min, 0/100 (v/v) buffer/acetonitrile from 30 to 35 min. Buffer solution is pH 3.0 aqueous solution adjusted by trifluoroacetic acid. The flow rate is set as 0.42 ml/min. Column temperature is set as 45° C., sample temperature is set as 25° C. Injection is 1.5 μL. Run time is 35 min. UV detector is set as 210 nm.

Example 1

Preparation of Treprostinil Monohydrate Form I Crystal 2-(((1R,2R,3aS,9aS)-2-hydroxy-1-((S)-3-hydroxyoctyl)-2,3,3a,4,9,9a-hexahydro-1H-cyclopenta[b]naphthalen-6-yl)oxy)acetonitrile (1.00 g, 2.7 mmol) was dissolved in 10 ml 2-propanol and followed by an addition of 4 ml potassium hydroxide solution (16% w/v), and stirred at 80° C. for 2 hours. Afterwards, the reaction mixture was slowly cooled to room temperature and quenched by hydrochloric acid solution, and concentrated to remove the 2-propanol, and 30 ml saturation sodium hydrogen carbonate aqueous solution with 30 ml ethyl acetate was added for extraction. The resulting Treprostinil was then extracted to the sodium hydrogen carbonate solution (pH value about 8.3) to form a homogenous solution at 20° C. Afterwards, the basic Treprostinil aqueous solution was acidified by slowly adding 9N phosphoric acid aqueous solution to adjust the pH value to about 3 in a decreasing rate of about 0.15 per minute, and then was stirred at 20° C. for 1 h until most of the crystal was precipitated. Thereafter, the resulting precipitate crystal was filtered and rinsed by 180 ml water, and then dried under high vacuum (about 0.01 Torr) at 20° C. for 2 hours to give 1.01 g Treprostinil monohydrate Form I crystal (yield: 91.9%). The XRPD and DSC results are the same as those shown in FIG. 5 and FIG. 6. UPLC analysis of the product shows that the purity is 100.0%. The Treprostinil ethyl ester and the Treprostinil dimers are non-detectable, and the other impurities are not found.

Example 2

Preparation of Treprostinil Monohydrate Form I Crystal 2-(((1R,2R,3aS,9aS)-2-hydroxy-1-((S)-3-hydroxyoctyl)-2,3,3a,4,9,9a-hexahydro-H-cyclopenta[b]naphthalen-6-yl)oxy)acetonitrile (1.00 g, 2.7 mmol) was dissolved in 10 ml 2-propanol and followed by an addition of 4 ml potassium hydroxide solution (16% w/v), and stirred at 80° C. for 2 hours. Afterwards, the reaction mixture was slowly cooled to room temperature and quenched by hydrochloric acid solution, and concentrated to remove the 2-propanol, and 25 ml saturation sodium hydrogen carbonate aqueous solution with 25 ml ethyl acetate was added for extraction. The resulting Treprostinil was then extracted to the sodium hydrogen carbonate solution (pH value about 8.3) to form a homogenous solution at 30° C. Afterwards, the basic Treprostinil aqueous solution was acidified by slowly adding 7N phosphoric acid aqueous solution to adjust the pH value to about 2.5 in a decreasing rate of about 0.17 per minute, and then was stirred at 30° C. for 1 h until most of the crystal was precipitated. Thereafter, the resulting precipitate crystal was filtered and rinsed by 200 ml water, and then dried under high vacuum (about 0.01 Torr) at 30° C. for 2 hours to give 1.03 g Treprostinil monohydrate Form I crystal (yield: 93.7%). The XRPD and DSC results are the same as those shown in FIG. 5 and FIG. 6. UPLC analysis of the product shows that the purity is 100.0%. The Treprostinil ethyl ester and the Treprostinil dimers are non-detectable, and the other impurities are not found.

Example 3

Preparation of Treprostinil Monohydrate Form I Crystal 2,2'-azanediyldiethanol 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate (1.00 g, 2.0 mmol) was dissolved in 20 ml saturation sodium hydrogen carbonate aqueous solution (pH value about 8.3) to form a homogenous solution at 25° C. Afterwards, the basic Treprostinil aqueous solution was acidified by slowly adding 9N phosphoric acid aqueous solution to adjust the pH value to about 2 in a decreasing rate of about 0.16 per minute, and then was stirred at 25° C. for 1 h until most of the crystal was precipitated. Thereafter, the resulting precipitate crystal was filtered and rinsed by 180 ml water, and then dried under high vacuum (about 0.1 Torr) at 25° C. for 3 hours to give 0.80 g Treprostinil monohydrate Form I crystal (yield: 97.2%). The XRPD and DSC results are the same as those shown in FIG. 5 and FIG. 6. UPLC analysis of the product shows that the purity is 100.0%. The Treprostinil ethyl ester and the Treprostinil dimers are non-detectable, and the other impurities are not found.

Example 4

Preparation of Treprostinil Monohydrate Form II Crystal 2-(((1R,2R,3aS,9aS)-2-hydroxy-1-((S)-3-hydroxyoctyl)-2,3,3a,4,9,9a-hexahydro-1H-cyclopenta[b]naphthalen-6-yl)oxy)acetonitrile (1.00 g, 2.7 mmol) was dissolved in 10 ml 2-propanol and followed by addition of 4 ml potassium hydroxide solution (16% w/v), and stirred at 80° C. for 2 hours. Afterwards, the reaction mixture was slowly cooled to room temperature and quenched by hydrochloric acid solution, and concentrated to remove the 2-propanol, and 30 ml potassium hydroxide solution with 30 ml ethyl acetate was added for extraction. The resulting Treprostinil was then extracted to the potassium hydroxide aqueous solution (pH value about 14) to form a homogenous solution at 20° C. Afterwards, the basic Treprostinil aqueous solution was acidified by quickly adding 9N phosphoric acid aqueous solution to adjust the pH value to about 2 in a decreasing rate of about 1.2 per minute, and stirred at 20° C. for 1 h until most of the crystal was precipitated. Thereafter, the resulting precipitate crystal was filtered and rinsed by 200 ml water, and then dried under high vacuum (about 0.01 Torr) at 20° C. for 2 hours to give 1.03 g Treprostinil monohydrate Form II crystal (yield: 93.7%). The XRPD and DSC results are the same as those shown in FIG. 8, and FIG. 9. UPLC analysis of the product shows that the purity is 100.0%. The Treprostinil ethyl ester and the Treprostinil dimers are non-detectable, and the other impurities are not found.

Example 5

Preparation of Treprostinil Monohydrate Form II Crystal 2-(((1R,2R,3aS,9aS)-2-hydroxy-1-((S)-3-hydroxyoctyl)-2,3,3a,4,9,9a-hexahydro-1H-cyclopenta[b]naphthalen-6-yl)oxy)acetonitrile (1.00 g, 2.7 mmol) was dissolved in 10 ml 2-propanol and followed by addition of 4 ml potassium hydroxide solution (16% w/v), and stirred at 80° C. for 2 hours. Afterwards, the reaction mixture was slowly cooled to room temperature and quenched by hydrochloric acid solution, and concentrated to remove the 2-propanol, and 20 ml sodium hydroxide solution with 20 ml ethyl acetate was added for extraction. The resulting Treprostinil was then extracted to the sodium hydroxide aqueous solution (pH value about 12) to form a homogenous solution at 10° C. Afterwards, the basic Treprostinil aqueous solution was acidified by quickly adding ION phosphoric acid aqueous solution to adjust the pH value to about 2.5 in a decreasing rate of about 1.9 per minute, and stirred at 10° C. for 1 h until most of the crystal was precipitated. Thereafter, the resulting precipitate crystal was filtered and rinsed by 250 ml water, and then dried under high vacuum (about 0.01 Torr) at 25° C. for 2 hours to give 1.02 g Treprostinil monohydrate Form II crystal (yield: 92.8%). The XRPD and DSC results are the same as those shown in FIG. 8, and FIG. 9. UPLC analysis of the product shows that the purity is 100.0%. The Treprostinil ethyl ester and the Treprostinil dimers are non-detectable, and the other impurities are not found.

Example 6

Preparation of Treprostinil Monohydrate Form II Crystal sodium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate (1.00 g, 2.4 mmol) was dissolved in 20 ml sodium hydroxide aqueous solution (pH value about 14) to form a homogenous Treprostinil aqueous solution at 10° C. Afterwards, the basic Treprostinil aqueous solution was acidified by quickly adding ION phosphoric acid aqueous solution to adjust the pH value to about 2 in a decreasing rate of about 2.4 per minute, and stirred at 10° C. for 1 h until most of the crystal was precipitated. Thereafter, the resulting precipitate crystal was filtered and rinsed by 180 ml water, and then dried under high vacuum (about 0.1 Torr) at 20° C. for 3 hours to give 0.97 g Treprostinil monohydrate Form U crystal (yield: 97.9%). The XRPD and DSC results are the same as those shown in FIG. 8, and FIG. 9. UPLC analysis of the product shows that the purity is 100.0%. The Treprostinil ethyl ester and the Treprostinil dimers are non-detectable, and the other impurities are not found.

Example 7

Preparation of the Mixture of Treprostinil Monohydrate Form I and Form II Crystals sodium 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetate (1.00 g, 2.4 mmol) was dissolved in 20 ml sodium hydrogen carbonate solution (pH value about 8.3) to form a homogenous Treprostinil aqueous solution at 20° C. Afterwards, the basic Treprostinil aqueous solution was acidified by adding 9N phosphoric acid aqueous solution to adjust the pH value to about 2 in a decreasing rate of about 0.32 per minute, and stirred at 20° C. for 1 h until most of the crystal was precipitated. Thereafter, the resulting precipitate crystal was filtered and rinsed by 200 ml water, and then dried under high vacuum (about 0.1 Torr) at 20° C. for 2 hours to give 0.99 g Treprostinil monohydrate crystal (yield: 90.1%), which comprises about 60% of Form I and 40% of Form II, and is substantially free of any other form of crystalline Treprostinil. The XRPD result is shown in FIG. 11. UPLC analysis of the product shows that the purity is 100.0%. The Treprostinil ethyl ester and the Treprostinil dimers are non-detectable, and the other impurities are not found.

What is claimed is:

1. A crystalline Treprostinil monohydrate Form I, characterized by having an X-ray powder diffraction (XRPD) pattern comprising its two strongest characteristic peaks at the following 2θ reflection angles: 5.43±0.2°, and 10.87±0.2°.

2. The crystalline Treprostinil monohydrate Form I of claim 1, wherein the XRPD pattern comprises its two strongest characteristic peaks at the following 2θ reflection angles: 5.43±0.2°, and 10.87±0.2°, and further comprises characteristic peaks at the following 2θ reflection angles: 12.30±0.2°, 16.34±0.2°, and 20.39±0.2°.

3. The crystalline Treprostinil monohydrate Form I of claim 1, characterized by having an X-ray powder diffraction (XRPD) pattern comprising its two strongest characteristic peaks at the following 2θ reflection angles: 5.43±0.2°, and 10.87±0.2°, and further having a differential scanning calorimetry (DSC) thermogram pattern comprising two major endothermic peaks, one with a peak maximum of 79.2±2° C., and the other with a peak maximum of 125.1±2° C.

4. A method for preparing the crystalline Treprostinil monohydrate Form I of claim 1, which comprises the steps of:
providing a basic Treprostinil aqueous solution;
adding phosphoric acid to the basic Treprostinil aqueous solution until the aqueous solution becomes acidic, having a pH value of about 2 to about 6, wherein a decreasing rate of the pH value is less than about 0.2 per minute; and
stirring until a precipitate is formed.

5. The method of claim 4, further comprising the steps of:
filtering out the precipitate and/or adding water for rinsing the precipitate, thereby isolating the crystalline Treprostinil monohydrate Form I; and
optionally drying the crystalline Treprostinil monohydrate Form I.

6. A crystalline Treprostinil monohydrate Form II, characterized by having an XRPD pattern comprising its two strongest characteristic peaks at the following 2θ reflection angles: 5.19±0.2°, and 10.40±0.2°.

7. The crystalline Treprostinil monohydrate Form II of claim 6, wherein the XRPD pattern comprises its two strongest characteristic peaks at the following 2θ reflection angles: 5.19±0.2°, and 10.40±0.2°, and further comprises characteristic peaks at the following 2θ reflection angles: 11.62±0.2°, 16.19±0.2°, and 20.14±0.2°.

8. The crystalline Treprostinil monohydrate Form II of claim 6, characterized by having an XRPD pattern comprising its two strongest characteristic peaks at the following 2θ reflection angles: 5.19±0.2°, and 10.40±0.2°, and further having a DSC thermogram pattern comprising two major endothermic peaks, one with a peak maximum of 73.8±2° C., and the other with a peak maximum of 125.1±2° C.

9. A method for preparing the crystalline Treprostinil monohydrate Form II of claim 6, which comprises the steps of:
providing a basic Treprostinil aqueous solution;
adding phosphoric acid to the basic Treprostinil aqueous solution until the aqueous solution becomes acidic, having a pH value of about 2 to about 6, wherein a decreasing rate of the pH value is more than about 0.6 per minute; and
stirring until a precipitate is formed.

10. The method of claim 9, further comprising the steps of:
filtering out the precipitate and/or adding water for rinsing the precipitate, thereby isolating the crystalline Treprostinil monohydrate Form II; and
optionally drying the crystalline Treprostinil monohydrate Form II.

* * * * *